US009532846B2

(12) United States Patent
Nakamura

(10) Patent No.: US 9,532,846 B2
(45) **Date of Patent: *Jan. 3, 2017**

(54) MEDICAL LIGHT-SOURCE DEVICE

(71) Applicants: ACP JAPAN CO., LTD., Tokyo (JP); Shoichi Nakamura, Higashichikuma-gun, Nagano (JP)

(72) Inventor: Shoichi Nakamura, Nagano (JP)

(73) Assignees: ACP JAPAN CO., LTD., Tokyo (JP); Shoichi Nakamura, Higashichikuma-gun, Nagano (JP)

( * ) Notice: Subject to any disclaimer, the term of this patent is extended or adjusted under 35 U.S.C. 154(b) by 128 days.

This patent is subject to a terminal disclaimer.

(21) Appl. No.: 14/502,265

(22) Filed: Sep. 30, 2014

(65) Prior Publication Data

US 2015/0015161 A1 Jan. 15, 2015

Related U.S. Application Data

(63) Continuation of application No. 13/520,065, filed as application No. PCT/JP2011/061884 on May 24, 2011, now Pat. No. 8,920,013.

(30) Foreign Application Priority Data

Nov. 17, 2010 (JP) ............................ 2010-007565 U
Jan. 13, 2011 (JP) ................................ 2011-004941

(51) Int. Cl.
*A61B 1/06* (2006.01)
*A61B 19/00* (2006.01)
(Continued)

(52) U.S. Cl.
CPC ............ *A61B 19/5202* (2013.01); *A61B 1/06* (2013.01); *A61B 90/30* (2016.02); *A61B 90/50* (2016.02);
(Continued)

(58) Field of Classification Search
CPC ....... A61B 19/5202; A61B 19/26; A61B 1/06; F21L 4/08; F21V 23/023; F21V 21/0816; H05B 33/0815; H05B 33/0854
See application file for complete search history.

(56) References Cited

U.S. PATENT DOCUMENTS

| | | | | | |
|---|---|---|---|---|---|
| 8,920,013 | B2 * | 12/2014 | Nakamura | A61B 19/5202 | 362/105 |
| 2007/0236955 | A1 * | 10/2007 | Fowler | F21V 29/02 | 362/554 |
| 2011/0105851 | A1 * | 5/2011 | Horvath | A61B 19/5202 | 600/249 |

* cited by examiner

*Primary Examiner* — Andrew Coughlin
*Assistant Examiner* — Meghan Ulanday
(74) *Attorney, Agent, or Firm* — Manabu Kanesaka

(57) ABSTRACT

A medical light-source device for securing a long illumination time required for operations in the medical field, has an LED illumination section including an LED element; a holder to put the LED illumination section on a head of the operator; a battery power supply section that supplies power to the LED illumination section; a charger having an AC adaptor capable of being connected to a commercial power supply for charging the battery power supply section; and a battery holding belt to put the battery power supply section and the charger on the body of the operator. The battery holding belt has a switch section to switch on/off the LED illumination section and to adjust intensity of illumination of the LED element; and a control section to control a constant current, which is associated with the intensity of illumination, supplied to the LED illumination section.

13 Claims, 15 Drawing Sheets

(51) Int. Cl.

| | |
|---|---|
| ***F21V 29/02*** | (2006.01) |
| ***F21L 4/00*** | (2006.01) |
| ***G02B 25/00*** | (2006.01) |
| ***G02B 25/02*** | (2006.01) |
| ***G02C 7/08*** | (2006.01) |
| ***G02C 11/04*** | (2006.01) |
| ***F21V 23/04*** | (2006.01) |
| ***F21L 4/08*** | (2006.01) |
| ***F21V 21/08*** | (2006.01) |
| ***F21V 23/02*** | (2006.01) |
| ***H05B 33/08*** | (2006.01) |
| *F21S 9/02* | (2006.01) |
| *F21W 131/20* | (2006.01) |
| *A61B 17/00* | (2006.01) |
| *F21Y 101/00* | (2016.01) |

(52) U.S. Cl.

CPC .................. *A61B 90/53* (2016.02); *F21L 4/00* (2013.01); *F21L 4/08* (2013.01); *F21V 21/0816* (2013.01); *F21V 23/023* (2013.01); *F21V 23/0414* (2013.01); *F21V 29/02* (2013.01); *G02B 25/004* (2013.01); *G02B 25/02* (2013.01); *G02C 7/088* (2013.01); *G02C 11/04* (2013.01); *H05B 33/0815* (2013.01); *H05B 33/0854* (2013.01); *A61B 2017/00734* (2013.01); *A61B 2090/309* (2016.02); *A61B 2090/502* (2016.02); *F21S 9/022* (2013.01); *F21W 2131/20* (2013.01); *F21Y 2101/00* (2013.01); *Y10S 362/80* (2013.01)

MEDICAL LIGHT-SOURCE DEVICE

CROSS-REFERENCES TO RELATED APPLICATIONS

The present application is a continuation application of U.S. patent application Ser. No. 13/520,065 and claims priority from PCT International Application No. PCT/JP2011/061884 filed May 24, 2011, and from Japanese Utility Model Application No. 2010-007565 filed Nov. 17, 2010; and Japanese Application No. 2011-004941 filed Jan. 13, 2011.

TECHNICAL FIELD

The present invention relates to a medical light-source device for irradiating a treatment target portion with light by an LED element in the medical treatment.

BACKGROUND ART

In medical light-source devices used in the medical treatment (including operations), it is general that a light source is placed in a rear upper position of an operator to irradiate the affected part. Further, it is also known that an operator such as a doctor wears a light source device on the body such as the head to perform the medical treatment.

In the medical treatment, a case arises that the operator wants to increase a quantity (illuminance) of light to irradiate the part targeted for the treatment. In such a case, the light quantity of the entire light is increased, but in the case where the light is secured and installed in the ceiling or the like of the treatment roan, there is a case that the quantity of light applied to the treatment target part is not always increased.

Accordingly, in order to enable the operator to secure required sufficient brightness to the treatment target part by increasing the quantity of light applied to the part, desirable is a medical light-source device of a type that the operator wears the device on the body. As such a medical light-source device, LED lights are used in terms of good luminous efficiency.

Patent Document 1 discloses a built-in battery type portable LED light provided with a clip capable of being put in a breast pocket or a brim of a cap of an operator. Further, Patent Documents 2 and 3 show configurations of a cap with a light in which the LED light is attached to the brim and a battery separate from the light is also stored in the cap.

PRIOR ART DOCUMENT

Patent Document

Patent Document 1: Japanese Patent Application Publication No. 2006-185755

Patent Document 2: Japanese Patent Application Publication No. 2008-210547

Patent Document 3: Japanese Patent Application Publication No. 2009-293146

DISCLOSURE OF INVENTION

Problems to be Solved by the Invention

However, in performing a medical operation, for example, depending on the treatment such as cutting and suture of a blood vessel or minute portion and the like, there are cases where it is required applying a higher quantity of light to the part only for a short time, but the conventional wearable LED light has a problem with the weight, is insufficient in the light source capacity of the battery, and is unsuitable for the treatment in the medical field.

In terms of the aforementioned respect, it is an object of the present invention to provide a medical light-source device capable of securing a long illumination time required for being used in operations in the medical field.

Means for Solving the Problem

To attain the above-mentioned object, a medical light-source device according to the invention is a medical light-source device that is worn on the body of an operator to apply light to a target portion of the medical treatment, and is characterized by having an LED illumination section comprised of an LED element, a holder to put the LED illumination section on the body of the operator, a battery power supply section that supplies power to the LED illumination section, a charger having an AC adaptor to charge the battery power supply section, and a battery holding belt to put the battery power supply section and the charger on the body of the operator, where the battery holding belt has means for being electrically connected to a terminal of the battery power supply section, and means for electrically connecting the AC adaptor to the battery power supply section.

Herein, the battery power supply section continues power supply to the LED illumination section without instantaneous interruption of supply occurring, when a commercial power supply fails or connection to the AC adaptor is interrupted.

Then, the holder is characterized by being a binocular loupe worn on the head of the operator. Further, the holder is characterized by being a cap or a head band put on the head of the operator. Then, the battery holding belt is characterized by being a belt wound around the waist of the operator.

Then, the LED illumination section is characterized by having installation means for enabling detachable attachment to the holder.

Then, the device is characterized by having a switch section that switches on/off the LED illumination section and that adjusts the intensity of illumination, and a control section that controls on/off of the LED illumination, while controlling the passage of a certain amount of current to the LED illumination section corresponding to designation of the intensity of illumination.

Further, the control section is characterized by controlling lighting of the LED illumination section by pulse driving with a duty ratio corresponding to designation of the intensity of illumination together with on/off of the LED illumination section.

Furthermore, it is a feature that the switch section and the control section are integrated to form a control unit, and that the control unit is held with the battery bolding belt.

Still furthermore, it is a feature that a fan to cool the LED illumination section is attached to the holder. Then, the fan is characterized by being incorporated into a housing of the LED illumination section to cool the LED element.

A medical light-source device according to the invention is a medical light-source device that is worn on the body of an operator to apply light to a target portion of the medical treatment, and is characterized by having an LED illumination section comprised of an LED element, a holder to put the LED illumination section on the body of the operator, a battery power supply section that supplies power to the LED illumination section, a control section provided with a current control circuit for controlling an average current value fed from the battery power supply section to the LED illumination section from a rated value to an increase value higher than the rated value, a first switch to light the LED illumination section, and a second switch to light the LED illumination section with an increase quantity of light, where the control section responds to ON operation of the second switch, and feeds the increase value of current to the LED illumination section only for a predetermined period.

Then, the predetermined period is characterized by being set based on a temperature increase time characteristic of the LED element due to passage of the increase value of current.

Further, the predetermined period is characterized by being set so that a temperature of the LED element within the predetermined period does not exceed a maximum allowable value, based on the temperature increase time characteristic of the LED element.

Then, the control section is characterized by halting feed of the increase value of current to the LED illumination section for a period required for the temperature of the LED element to fall below the rated allowable value after the increase value of current is fed to the LED illumination section, even when ON operation of the second switch is performed.

Further, it is a feature that the first switch, the second switch and the control section are integrated to form a control unit, and that the control unit is held with the battery holding belt.

Furthermore, the control section is characterized by performing both control of the LED illumination section and control of charging the battery power supply section with the charger connected.

Then, it is a feature that the battery power supply section is comprised of a plurality of batteries, and that the battery holding belt holds the batteries with the batteries embedded in the belt.

A medical light-source device according to the invention is a medical light-source device that is worn on the body of an operator to apply light to a target portion of the medical treatment, and is characterized by having an LED illumination section comprised of an LED element, a holder to put the LED illumination section on the body of the operator, a battery power supply section that supplies power to the LED illumination section, a control section provided with a current control circuit for controlling an average current value fed from the battery power supply section to the LED illumination section from a rated value to an increase value higher than the rated value, a first switch to light the LED illumination section, at least one second switch to light the LED illumination section with an increase quantity of light, and a temperature sensor that detects a temperature of the LED element, where the control section responds to ON/OFF operation of the second switch, and feeds the increase value of current to the LED illumination section within a range in which the temperature of the LED element does not exceed a beforehand set maximum allowable value.

Then, it is a feature that the increase value higher than the rated value is set in a plurality of stages, and that the LED illumination section is configured to apply light of light quantities in the plurality of stages more than a normal quantity of light of the time ON operation of the first switch is performed, by the second switch being operated.

Further, the control section is characterized by halting feed of the increase value of current to the LED illumination section in the case where the temperature of the LED element does not reduce from the beforehand set maximum allowable value by a predetermined value or more, even when ON operation of the second switch is performed.

A medical light-source device according to the invention is a medical light-source device that is worn on the body of an operator to apply light to a target portion of the medical treatment, and is characterized by having an LED illumination section comprised of an LED element, a holder to put the LED illumination section on the body of the operator, a battery power supply section that supplies power to the LED illumination section, an acceleration sensor provided in the holder, and a control section that controls the passage of current to the LED illumination section when the LED illumination section is on, where the control section performs control for reducing illuminance of the LED illumination section when the acceleration sensor detects acceleration of a predetermined value or more.

Then, the control section is characterized by halting the passage of current to the LED illumination section when the acceleration sensor detects acceleration of the predetermined value or more.

Advantageous Effect of the Invention

According to the invention, by holding the battery power supply section that supplies power to the LED illumination section with the belt wearable on part of the body, it is possible to secure the required battery power supply section on the body of the operator. By this moans, provided is the medical light-source device exploiting superiority of LED light that does not hurt the treatment target portion by heat even when the light is applied for a long time.

Further, according to the invention, in the light-source device by the LED element wearable on the body of the operator, in the case where the need for particularly increasing the quantity of light arises, by feeding the current of the maximum value or less exceeding the rated value (continuous rated value) for a predetermined period within the range in which the LED element does not deteriorate due to the effect of heating, it is possible to increase the quantity of light without using any complicated configuration. Accordingly, a medical light-source device smaller in size is provided without needing a large capacity of battery power supply section and particular heat dissipation measures.

Furthermore, according to the invention, by the acceleration sensor sensing a notion of the operator, provided is the medical light-source device which increases illuminance during the medical treatment, while reducing illuminance during the time other than the treatment, and is thereby able to suppress consumption of the battery power supply.

BEST MODE FOR CARRYING OUT THE INVENTION

Embodiments of the invention will be described below with reference to drawings.

Figure 1:
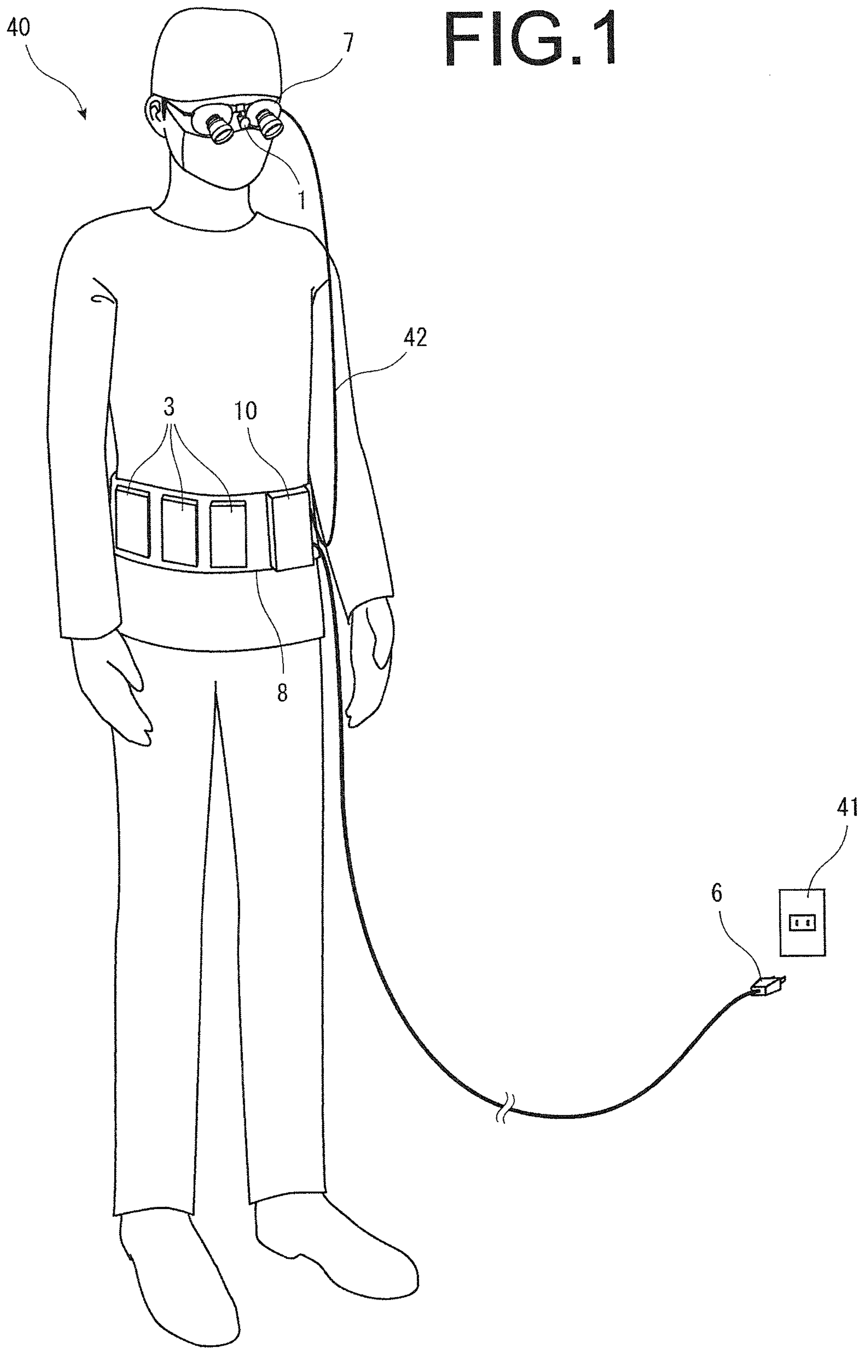
FIG. 1 is an explanatory view showing a state of wearing a medical light-source device according to an Embodiment of the invention.

FIG. 1 is a view to explain a medical light-source device according to an Embodiment of the invention, and shows a case that an operator wears the device. An LED illumination section 1 is held by a binocular loupe worn by an operator 40 and is worn on the head of the operator 40. Accordingly, in this Example, the binocular loupe functions as a holder 7.

Then, as part of the body of the operator 40, in this example, a battery holding belt 8 is wound around the waist. To the battery holding belt 8 are attached a plurality of rechargeable battery power supply sections 3 that are mutually connected, and a control unit 10. The battery power supply sections 3 are connected to the control unit 10, and the control unit 10 supplies an adequate driving current to the LED illumination section 1 through a code 42 to control illumination operation.

In addition, the battery power supply sections 3 are not limited to a plurality of sections, and there is a case that a single large-sized battery power supply section 3 is allowed as long as the section 3 is capable of supplying stable power to the LED illumination section 1 over a long time, but even such heavy battery power supply sections are capable of being worn on part of the body by being attached to the battery holding belt 8.

Further, the control unit 10 performs charging control on the battery power supply sections 3 when a charger 6 with a plug inserted therein is connected to an outlet 41, and is capable of performing illumination operation by the LED illumination section 1 while charging the battery power supply section 3.

Thus, the operator finishes the medical treatment while holding the battery power supply sections 3 with the battery holding belt 8 attached to part of the body, and the device is suitable as a medical light-source device required of long-duration treatment. Further, when necessary, it is possible to perform operation while charging. Moreover, stable illuminance is obtained since the passage of current to the LED illumination section 1 is controlled by the control unit 10 attached to the battery holding belt 8, and in terms of the respect, the light-source device is suitable for medical care.

In this way, in the medical light-source device, the battery power supply sections are attached to the battery holding belt, and the operator wears the battery holding belt on part of the body, and is thereby capable of carrying either of the battery power supply section comprised of a large-sized battery and the battery power supply section comprised of a number of small-sized batteries. Therefore, it is possible to ensure the large power supply capacity enabling the operator to obtain sufficient illumination time in performing the medical treatment.

Figure 2:
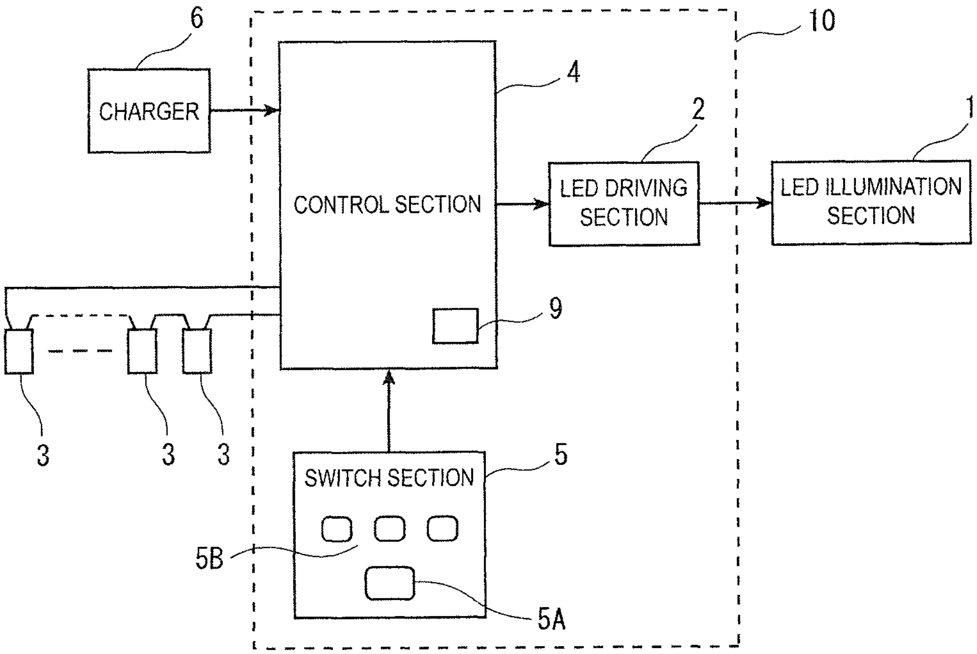
FIG. 2 is a block diagram illustrating an electric circuit of the medical light-source device according to the Embodiment of the invention.

Each configuration of the medical light-source device as shown in FIG. 1 will be described specifically. FIG. 2 is a block diagram illustrating an electric circuit, and is comprised of the LED illumination section 1, an LED driving section 2, a plurality of rechargeable lithium ion battery power supply sections 3 mutually connected in series or parallel, a control section 4 comprised of an MPG board, for example, a switch section 5 provided with a power supply ON/OFF switch 5A and three selection switches 5B to adjust the intensity of illumination of the LED illumination section 1 to high, middle and low, and an AC adopter as the charger 6 to charge the battery power supply sections 3.

In this electric circuit, the LED driving section 2, control section 4 and switch section 5 are integrated to form the control unit 10. Then, the LED illumination section 1 and battery power supply sections 3 are configured while being separate from the control unit 10, and are electrically connected to the control unit 10 when operating. Further, the charger 6 is capable of being connected to the control unit 10 when necessary.

The control section 4 controls the illumination operation of the LED illumination section 1 through the LED driving section 2, when a power supply ON signal is input from the switch section 5 by switching on the power supply ON/OFF switch 5A. Then, when an illumination intensity selection signal is input from the switch section 5 by operating the selection switch 5B, the control section 4 controls the LED driving section 2 so that a constant current associated with the intensity of light designated at this point is applied to the LED illumination section 1.

Figure 6:
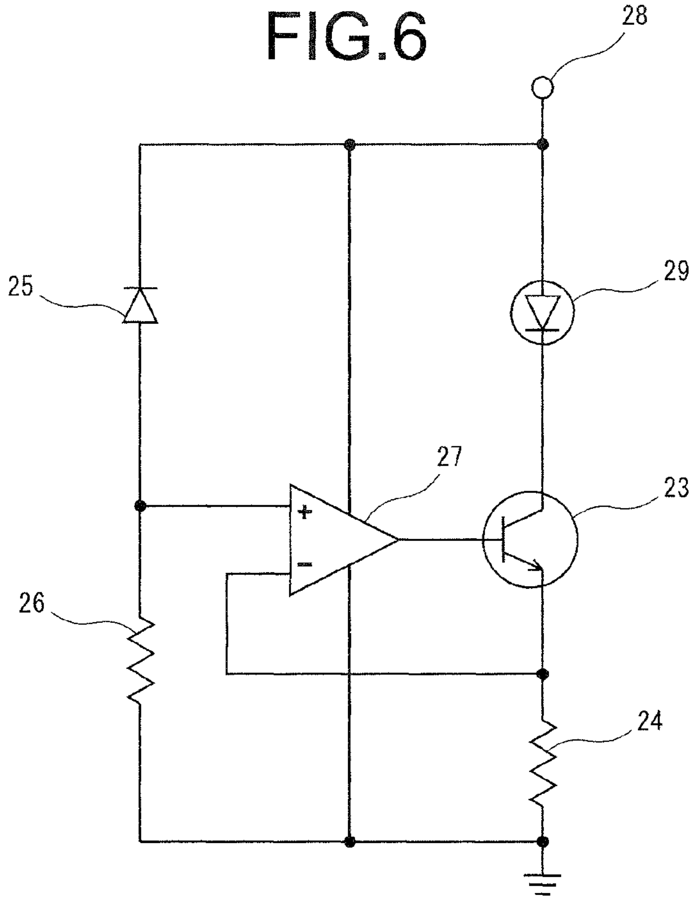
FIG. 6 is a configuration explanatory view of an LED driving section by constant-current driving according to the Embodiment of the invention.

FIG. 6 shows a configuration of the LED driving section 2 that drives the LED illumination section 1 with a constant current. In FIG. 6, the LED driving section 2 is comprised of a driving transistor 23 connected at its collector side to an LED 29 of the LED illumination section 1, a resistance 24 connected to the emitter side of the transistor 23 with the other end grounded, a constant-voltage diode 25 connected to a power supply terminal 28 in parallel with the LED 29, a resistance 26 connected at is one end to the constant voltage diode 25 with the other end grounded, and an operation amplifier 27 in which the + input side thereof is connected to the middle point of the constant-voltage diode 25 and the resistance 26, the − input side thereof is connected to the middle point of the emitter side of the transistor 23 and the resistance 24, and the output side thereof is connected to the base side of the transistor 23. Further, the other end of the LED 29 of the LED illumination section 1 connected to the collector side of the transistor 23 is connected to the power supply terminal 28 to which is supplied power of the buttery power supply sections 3.

In the LED driving section 2 as shown in FIG. 6 with such a configuration, when the control section 4 supplies the voltage associated with the designated illumination intensity based on the operation of the selection switch 5B to the power supply terminal 28, the transistor 23 carries the base voltage by the operation amplifier 27 and is ON, and the current is fed to the LED 29. Meanwhile, the current is also fed to the path of the constant-voltage diode 25 and the resistance 26, and the terminal voltage of the resistance 26 applied to the + input side of the operation amplifier 27 is constant.

Then, when the current passing through the LED 29 exceeds a set value, the current passing through the resistance 24 also increases, the terminal voltage of the resistance 24 applied to the − input side of the operation amplifier 27 increases, the operation amplifier 27 therefore controls the base voltage to turn off the transistor 23, and the current is thereby not fed to the LED. This operation is always repeated, and it is thereby possible to perform constant-current operation.

Controlling the emission operation of the LED illumination section 1 is not limited to the above-mentioned constant-current driving scheme, and may be a pulse driving scheme for controlling a duty ratio corresponding to designation of the illumination intensity with a switch device on the circuit such as, for example, a transistor, MOSFET, etc. and thereby controlling a current fed to the LED illumination section 1.

Figure 7:
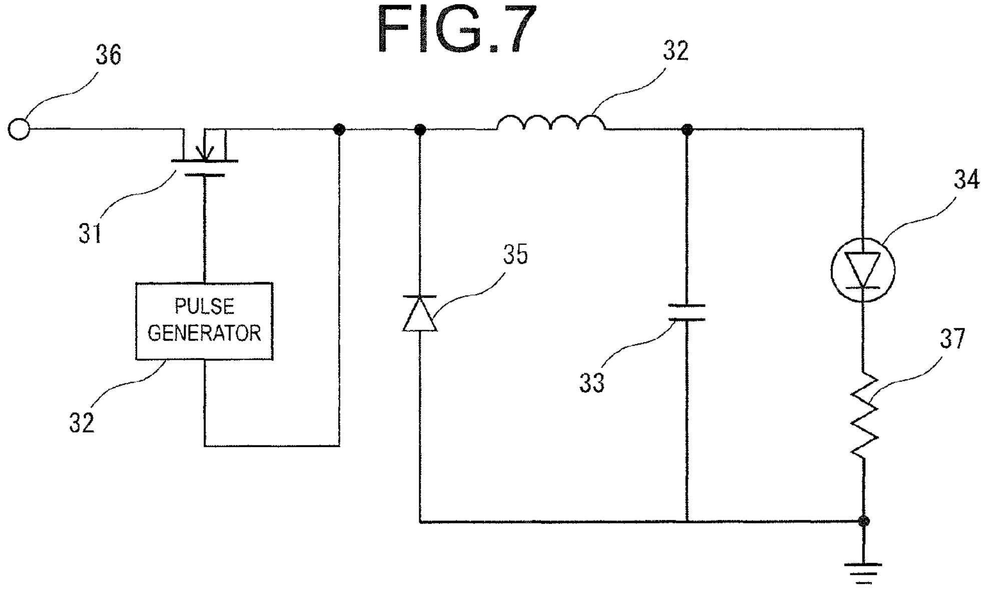
FIG. 7 is an explanatory view of a configuration of the LED driving section by a pulse driving scheme according to the Embodiment of the invention.

FIG. 7 shows a configuration of the LED driving section 2 by the pulse driving scheme. In FIG. 2, for example, MOSFET is used as a switch device 31, and is connected so that a PWM (Pulse Width Modulation) signal from a pulse generator 32 is input to the gate side thereof. When the PWM signal becomes a high level, the switch device 31 is turned on, the current flows from the input side connected to the power supply terminal 36, to which the voltage of the battery power supply section 3 is applied, to the load side.

To the load side of the switch device 31 are connected an LED 34 of the LED illumination section 1 and a resistance 37 which is grounded. In the prior stage, a smoothing circuit comprised of a coil 32 and a capacitor 33 is provided, and it is configured that a pulse output by switching operation is averaged and output. In the stage before the coil 32, a diode 35 is provided to continue to supply a current to the coil 32 when the switch device 31 is switched off. By this means, by controlling the on time (off time) of the switch device 31, it is possible to efficiently adjust the current fed to the LED illumination section 1. Accordingly, in this case, the control section 4 is capable of adjusting brightness of the LED illumination section 1 by performing control for changing the duty ratio of the pulse generator 32.

In FIG. 2, the control section 4 checks the power supply capacity of the battery power supply sections 3, and when the section 4 detects a reduction in the voltage, lights an indicator 9 to warn. Then, when the charger 6 is connected to the control unit 10, the section 4 controls current supply to charge the battery power supply sections 3 from the charger 6, and Charges the battery power supply sections 3.

The LED light is low in the caloric value, and has the advantage that an irradiation target substance is hard to undergo the effect by heat when the substance is irradiated for a long time. Accordingly, in the medical operation continuing over several hours, the device does not hurt tissue of the body, and is suitable as a light-source device of the medical operation.

Figure 3:
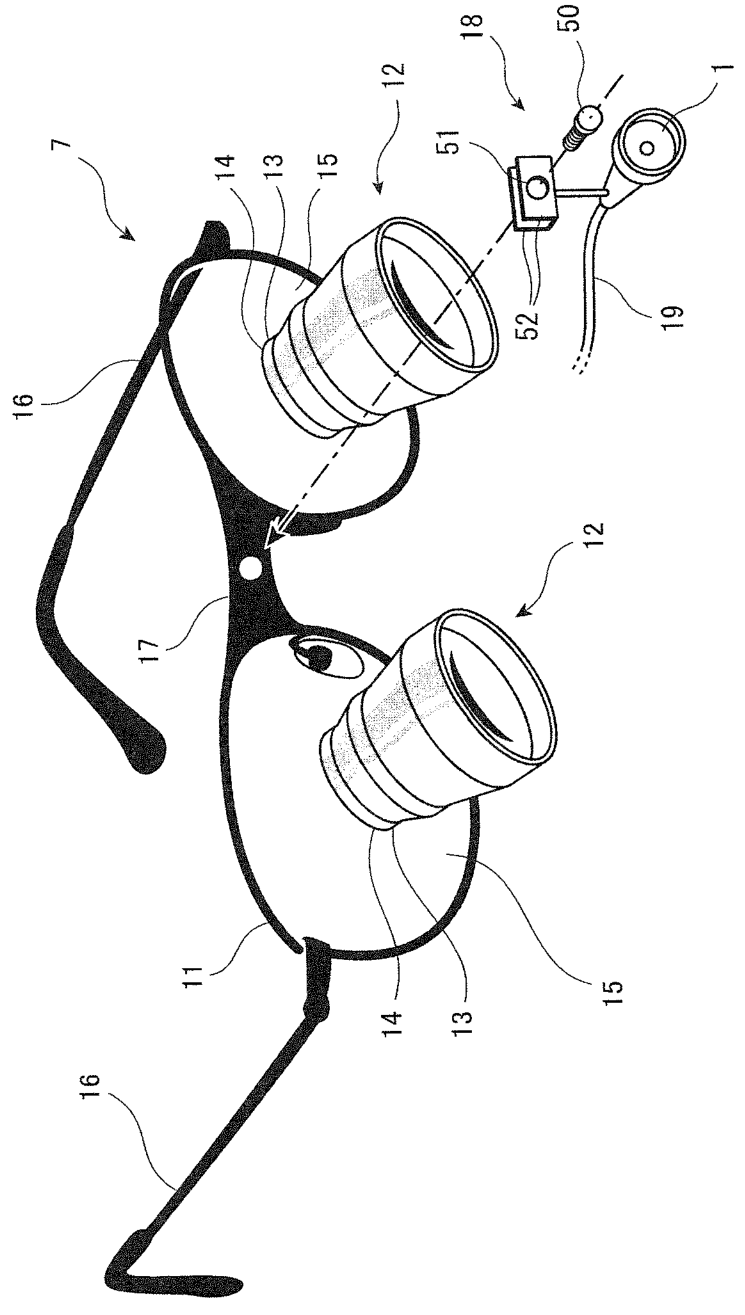
FIG. 3 is an explanatory view when a holder of the medical light-source device according to the Embodiment of the invention is a binocular loupe.

In order for an operator to wear the LED illumination section 1 on the head of the operator, in the example as shown in FIG. 3, as in the case of FIG. 1, the LED illumination section 1 is attached using a binocular loupe as the holder 7. The binocular loupe is widely used in various fields such as the medical field, precision working and jewel processing as means for enlarging a local viewing target substance at hand to visually identify, and is comprised of a main glasses attachment frame 11 with the sane structure as glasses, binocular loupe bodies 12 (main glasses) to enlarge an image of a working subject, main glasses attachment portions 13 to attach the binocular loupe bodies 12 to the main glasses attachment frame 11, focus adjustment sections 14 for enabling compensation for eyesight of a precision operator, main glasses attachment carrier lenses 15 to attach the binocular loupe bodies, and frame temple portions 16 to be worn on the precision operator.

When the LED illumination section 1 is attached to the binocular loupe, the LED illumination section 1 is attached to a bridge 17 of the binocular loupe with attachment means 18. The attachment means 18 is comprised of a pair of opposite plates 52 that sandwich the bridge 17 of the binocular loupe, screw holes 51 provided in respective opposite plates 52, and a screw 50, the screw 50 penetrates a though hole formed in the bridge 17 of the binocular loupe and the screw holes 51 of the opposite plates 52 and is secured, and the LED illumination section 1 is attached to the binocular loupe.

Then, a current-carrying code 19 from the control unit 10 to the LED illumination section 1 is held in the main glasses attachment frame 11 and the frame temple portions 16 with appropriate means, not shown, and is thereby prevented from hanging in front of the body of the operator.

By thus combining the binocular loupe and the LED illumination section 1, it is possible to achieve a deeper deep focus depth required of the binocular loupe.

Figure 4:
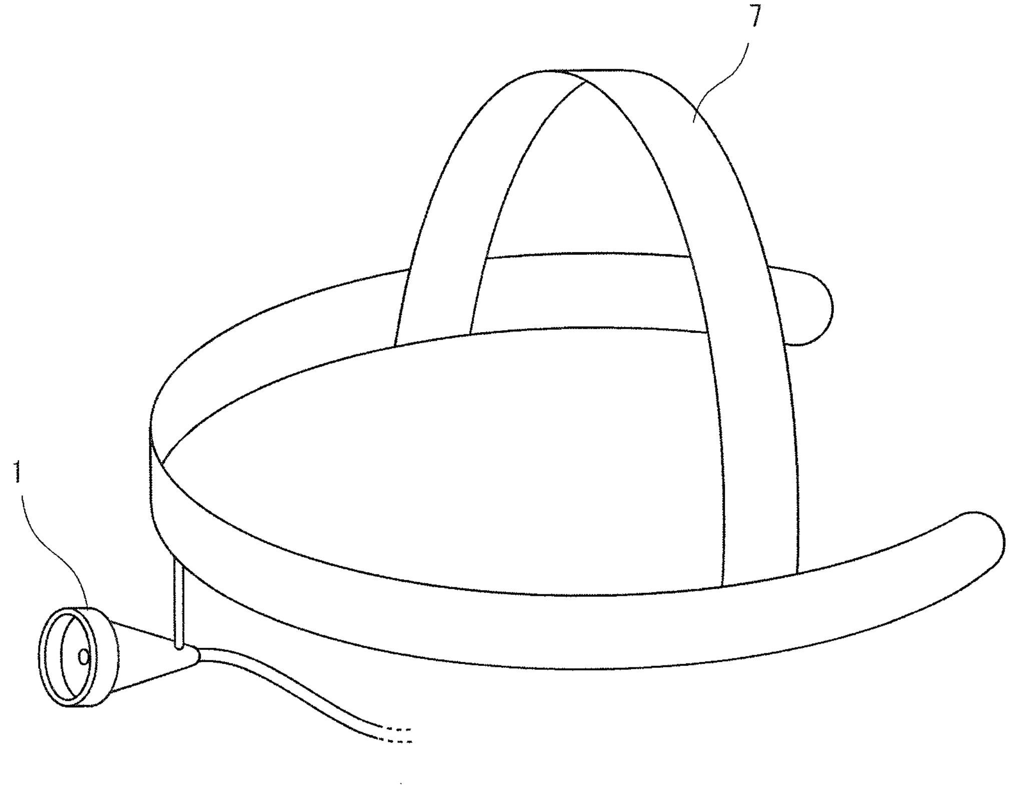
FIG. 4 is an explanatory view when a holder of the medical light-source device according to the Embodiment of the invention is a head band.

The holder 7 is not limited to such a binocular loupe, and may be a cap or a head band. FIG. 4 shows an example where a head band is used as the holder 7, and the LED illumination section 1 is attached to the head band. The head band is made of a resin member, is held on the head of the operator by its elasticity and can thereby be fixed. The head band is not limited to such a configuration, and also as the material, adopts various nodes such as cloth and rubber.

Further, in the head band exemplified in FIG. 4, although the LED illumination section 1 and the head band are integrated, as in the example of the binocular loupe, by constructing a configuration in which the LED illumination section 1 is detachable with respect to the head band as appropriate with attachment means such as the attachment means 18 using the screw 50 as shown in FIG. 3 and a clip, it is possible to also use general-purpose head bands used in various manners as the holder 7.

In this way, by the LED illumination section 1 being worn on the head of the operator, even when the operator changes the working position, it is possible to ensure sufficient illuminance and irradiation range at hand.

In addition, as described above, the LED illumination section 1 may be attached to a head band, or may be configured integrally with a head band. Further, the electric code from the LED illumination section 1 is connected to the control unit 10, and is preferably connected via a code reel to wind the code.

Figure 5:
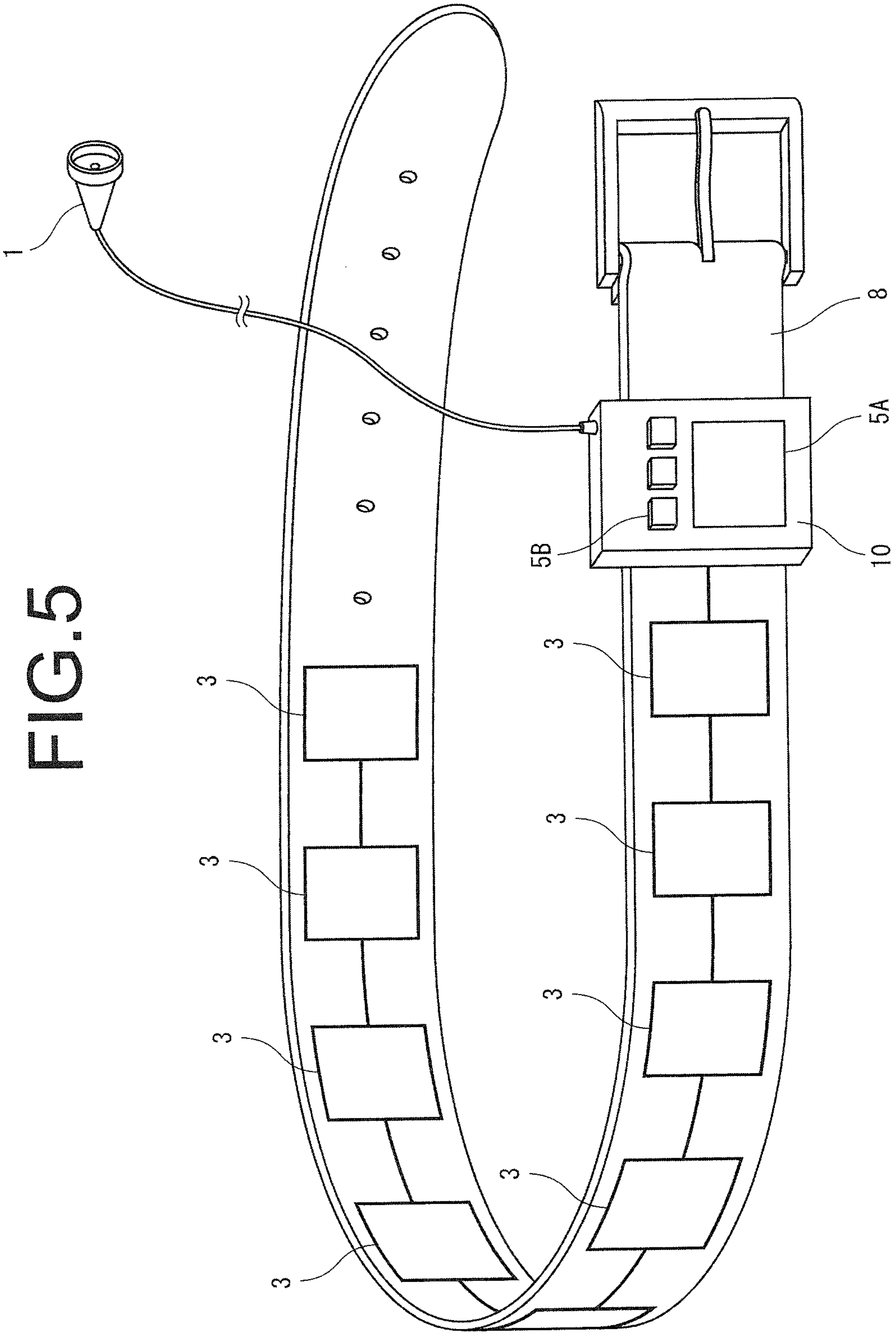
FIG. 5 is an explanatory view of a battery holding belt of the medical light-source device according to the Embodiment of the invention.

FIG. 5 shows the battery holding belt 8 that holds the battery power supply sections 3 for enabling the operator to wear the battery power supply sections 3 on part of the body. As described previously, although there is the case of a single battery power supply section 3, as in FIG. 1, also in this example, a plurality of battery power supply sections 3 is connected to one another with a code reel, and is further connected to the control unit 10 with the code reel, and the battery power supply sections 3 and the control unit 10 are thereby arranged circularly on the battery holding belt 8. As shown in the figure, the battery holding belt 8 holds a plurality of battery power supply sections 3 with the sections 3 embedded in the belt. By this means, the operator winds the battery holding belt 8 around the waist, is capable of wearing the battery power supply sections 3 and the control unit 10 on the body together with the LED illumination section 1 during the medical treatment, and is able to perform the medical treatment while operating the power supply ON/OFF switch 5A and the selection switches 5B to adjust the illumination intensity to three ways of high, middle and low disposed on the front of the control unit 10.

Further, it is also possible to always connect the charger 6 to the control unit 10. In this case, since the control section 4 concurrently performs both control of the LED illumination section 1 and control of charging the battery power supply sections 3, the light is applied from the LED illumination section 1 while charging, and it is thereby possible to support work continuing for a long time.

In the above-mentioned medical light-source device, the battery power supply sections 3 are worn on the body of the operator with the battery holding belt, both of a large-sized battery and a number of small-sized batteries can thus be carried, and it is thereby possible to secure the large power supply capacity enabling the operator to obtain sufficient illumination time in performing the treatment in the medical field.

Meanwhile, as well as securing the large capacity of power supply by wearing the battery on the body, by suppressing power consumption in the battery power supply section, sufficient illumination time is also obtained in performing the treatment in the medical field.

With attention directed toward the respect that the working time requiring a high degree of accuracy with the need for particularly increasing illuminance is limited in an operation continuing over a long time in the medical field, by limiting a period in which the LED element emits with high output, it is also possible to secure the long illumination time required in the medical field with a relatively small-sized battery.

Figure 8:
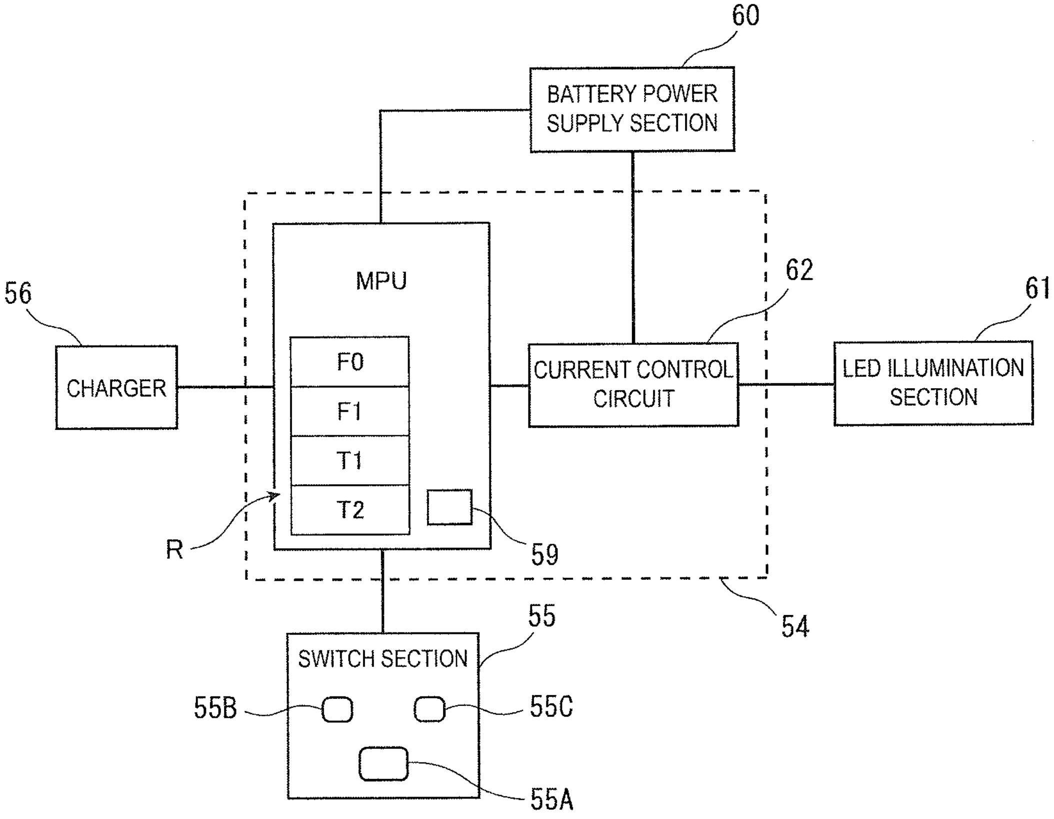
FIG. 8 is a block diagram illustrating an electric circuit of a medical light-source device according to Embodiment 2 of the invention.

From such a viewpoint, a medical light-source device according to Embodiment 2 of the invention causes the LED element to emit with high output by operation of an operator when the need arises, and limits the period with a timer. FIG. 8 is a block diagram illustrating a circuit configuration of the medical light-source device according to Embodiment 2, and is comprised of an LED illumination section 61 having an LED element, a control section 54 provided with a microprocessor unit MPU and a current control circuit 2, a switch section 55, a battery power supply section 60 comprised of a plurality of connected rechargeable batteries, and an AC adopter as a charger 56 to charge the battery power supply section 60. Then, the microprocessor unit (hereinafter, simply referred to as MPU) of the control section 54 is programmed with processing procedures for controlling the peripheral devices.

The switch section 55 is comprised of a first switch 55A to light the LED illumination section 61, and second switches 55B, 55C to light the LED illumination section 61 with increase light quantities. When the second switches 55B, 55C are operated, the control section 54 controls the current control circuit 62 so as to change the average current value fed to the LED illumination section 61 from a rated value to an increase value higher than the rated value.

In this Embodiment, two switches 55B, 55C are provided to enable a light quantity to increase to be selected in two ways, and the operator is capable of selecting a light quantity to increase from between high and low as appropriate.

Further, the control section 54 checks the power supply capacity of the battery power supply section 60, and when the section 54 detects a reduction in the voltage, lights an indicator 59 to warn. Then, when the charger 56 is connected to the control section 54, the section 54 controls current supply to charge the batteries in the battery power supply section 60 from the charger 56.

Figure 9:
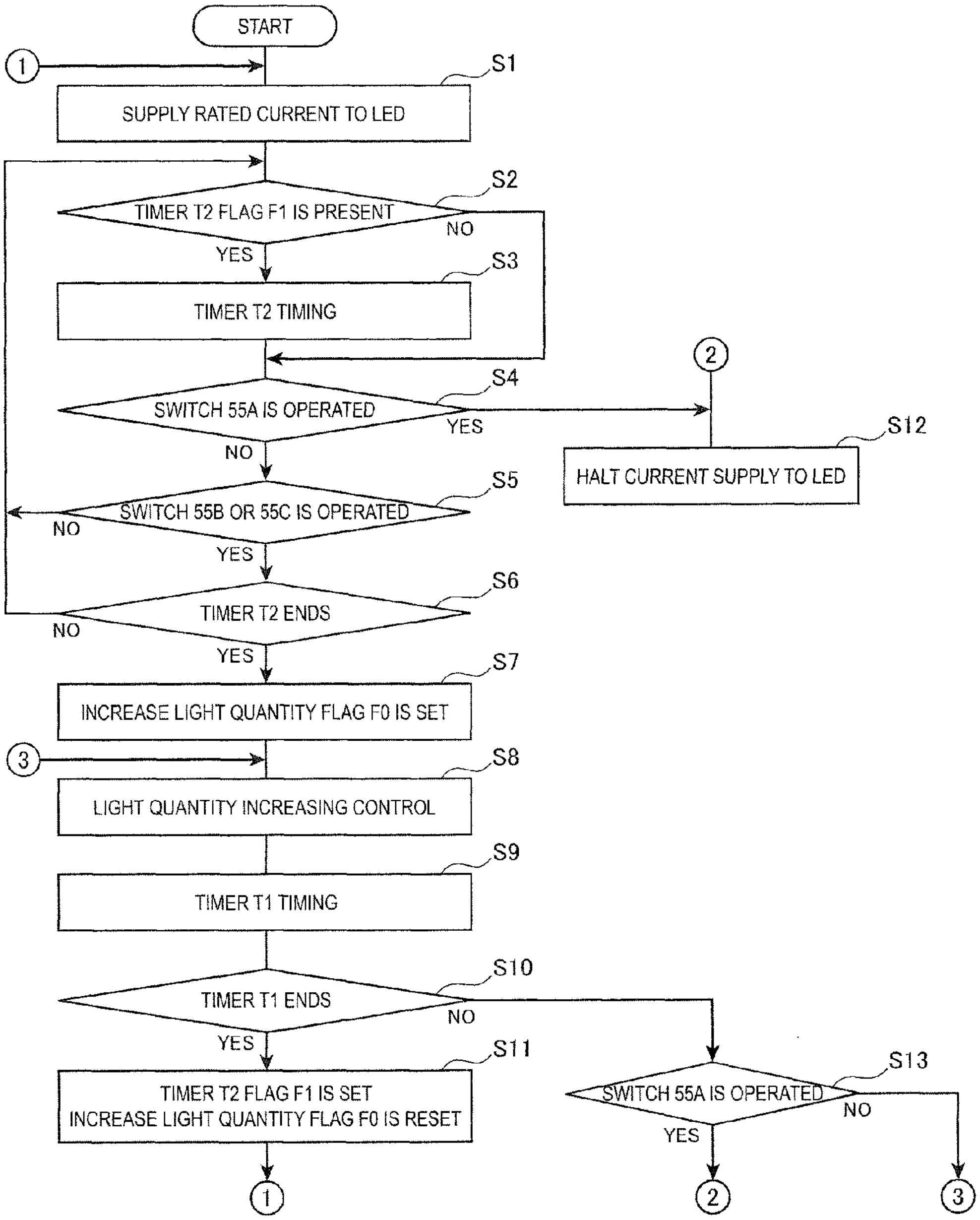
FIG. 9 is a flowchart illustrating a processing procedure for a control section to control lighting of an LED illumination section according to Embodiment 2 of the invention.

FIG. 9 is a flowchart illustrating a processing procedure for controlling lighting of the LED illumination section 61 by the MPU in the control section 54. The MPU starts the processing procedure when the switch 55A is operated, and controls the current control circuit 62 so as to supply a rated value of current to the LED illumination section 61 (step S1). At this point, the current control circuit 62 is controlled by the MPU so that the average current value fed from the battery power supply section 60 to the LED illumination section 61 is a rated value.

Then, the MPU checks whether a register R is set for a timer T2 flag (step S2), and when the flag is not set, proceeds to step S4, while when the flag is set, adding a timer value to the timer T2 of the register R and performing timer timing (step S3). The processing in step S2 and step S3 will be clarified later. Herein, the timer flag T2 is not set, and the MPU performs the processing of step S4.

In step S4, the MPU acquires a signal from the switch section 55, checks the operation of the switch 55A, and when the second operation of the switch 55A from the start is not performed, checks the operation of the switch 55B or switch 55C (step S5). When the MPU identifies the operation of either the switch 55B or 55C, the MPU checks whether the timer T2 clocking in the register R provided inside is finished (step S6). In this case, the clocking operation of the timer T2 is not performed, and the MPU proceeds to next step S7.

In step S7, the MPU sets the register R for an increase light quantity flag F0, and in the increase light quantity flag F0 is written data to identify the switch 55B or switch 55C that is operated.

Then, based on the content of the increase light quantity flag F0, the MPU controls the current control circuit 62 to increase the illumination quantity of the LED illumination section 61 corresponding to the operated switch 55B or switch 55C (step S8). By this light quantity increasing control, the average current value fed to the LED illumination section 61 is changed from the rated value, and the current of an increase value higher than the rated value is fed. Then, when either the switch 55B or 55C is operated, the supply current to the LED illumination section 61 is of an increase value exceeding the rated value, and the current fed when the switch 55B is operated is made higher than the current fed when the switch 55C is operated.

When the current of the increase value higher than the rated value is fed to the LED illumination section 61, the LED element generates heat corresponding to the temperature increase characteristic, and develops a malfunction, and therefore, the time, during which the MPU feeds the current of the increase value higher than the rated value to the LED illumination section 61, is determined to be a predetermined period based on the temperature increase characteristic of the LED element.

Further, more specifically, the predetermined period is set so that the temperature of the LED element within the predetermined period does not exceed a maximum allowable value based on the temperature increase time characteristic of the LED element.

Accordingly, after performing control of the increase light quantity, the MPU adds a timer value to the timer T1 of the register R to perform time T1 timing (step S9). Then, as a result of addition, the MPU determines whether the value of the timer T1 reaches a predetermined determination value, and thereby determines whether the timer time exceeds the predetermined period (step S10). At this point, a larger amount of current is fed when the switch 55B with a larger increase light quantity is operated, the predetermined period is thereby set to be shorter, and the MPU is programmed so as to change a determination value of the value of the timer T1 corresponding to the content of the increase light quantity flag F0 set on the register R.

For example, for the light quantity when the switch 55B is operated, the predetermined period is set at 20 minutes as the timer time since the light quantity is increased by 40% as compared with the time of normal rated current supply. Meanwhile, when the switch 55C is operated, the predetermined period is set at 30 minutes as the timer time since the light quantity of the LED illumination section 61 is increased by 30% as compared with the time of normal rated current supply.

In step S10, when the MPU determines that the value is within the timer time, the MPU identifies that the switch 55A is not performed (step S13), and repeats the operation of from step S8. In other words, the MPU is in an increase light quantity control mode. In this mode, when the MPU identifies that the switch 55A is operated (step S13), the MPU controls the current control circuit 62 to halt the supply of current to the LED illumination section 61, and finishes lighting of the LED illumination section 61 (step S12). At the same time, the content of the register R is all cleared, and is in the initial state.

Meanwhile, when the MPU identifies an end of the timer time T1 in step S10, the MPU sets the register R for a timer T2 flag F1, while clearing the increase light quantity flag F0 (step S11), then shifts to the processing of step S1, switches the current supplied to the LED illumination section 61 to the rated value, finishes control of the increase light quantity, and performs the operation of from step S2.

Thus, in a certain period after increasing the light quantity of the LED illumination section 61 and feeding again the rated value of current to return to the normal light quantity, the MPU halts feed of the increase value of current even when the switch 55B or switch 55C is operated. This certain period is set at the time required for the temperature of the LED element to fall below the rated allowable value after the increase value of current is fed to the LED illumination section 61.

Accordingly, in performing the processing of step S2 in the state in which the light quantity of the LED illumination section 61 is increased and then, is returned to the normal light quantity by feeding again the rated value of current, since the MPU sets the register R1 for the timer T2 flag F1 in the processing in prior step S11, the MPU adds a timer value to the timer T2 of the register R and performs timer T2 timing in the processing in next step S3.

Hereinafter, the MPU controls emission of the normal light quantity while performing timing of the timer T2, unless the MPU is instructed to halt driving of the LED illumination section 61 by operation of the switch 55A in step S4.

Then, when the MPU identifies that the switch 55B or 55C is operated in step S5, the MPU determines whether the value of the timer T2 reaches the predetermined determination value in next step S6, and thereby determines whether the timer T2 time exceeds the predetermined period. The predetermined period at this point is the above-mentioned time required for the temperature of the LED element to fall below the rated allowable value after the increase value of current is fed to the LED illumination section 61.

Accordingly, when the timer T2 exceeds the predetermined period, the MPU clears the timer T2, proceeds to step S7, and sets the register R for the increase light quantity flag F0 to perform increase light quantity control. Meanwhile, when the timer T2 does not reach the predetermined period, the MPU does not perform increase light quantity control, performs the processing of from step S2, and performs timing of the timer T2 while controlling emission of the normal light quantity.

By a series of control due to such a processing procedure, when the switch 55B or 55C is operated in the state in which the rated value of current is supplied to the LED illumination section 61, the MPU feeds the increase value of current exceeding the rated current within the timer time that guarantees that the LED element is prevented from deteriorating by heat in the LED illumination section 61, and achieves a high luminous flux (increased light).

Figure 10:
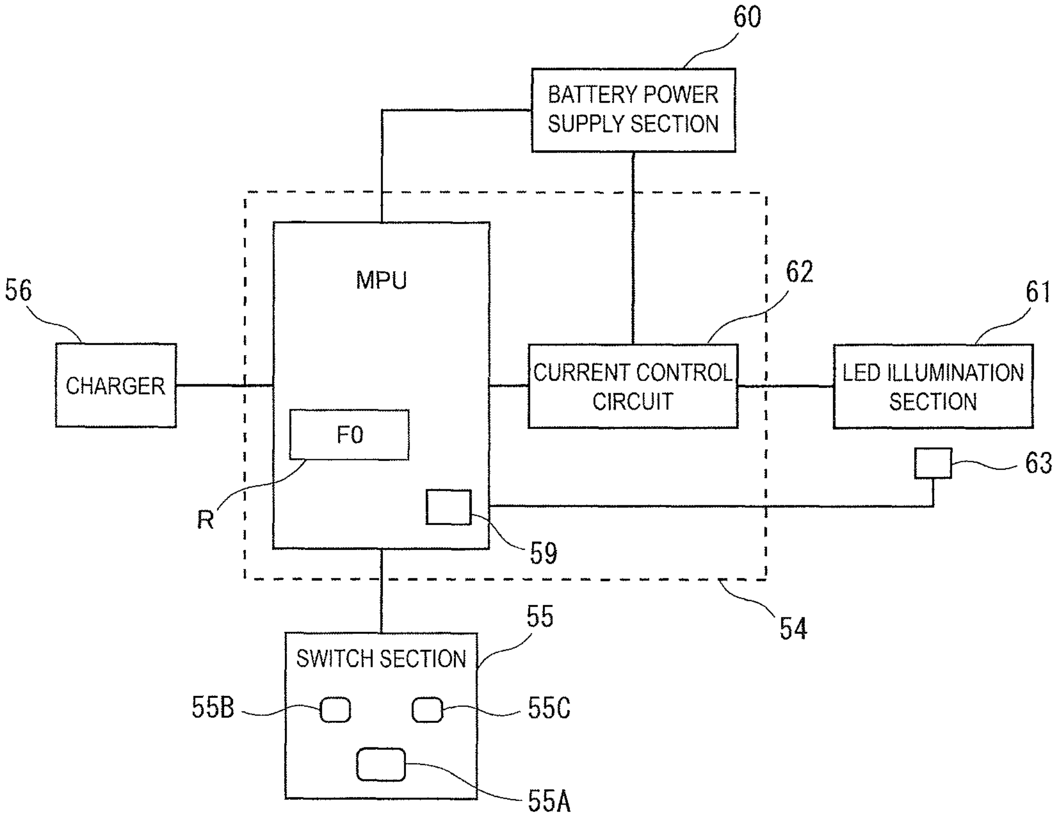
FIG. 10 is a block diagram illustrating an electric circuit of a medical light-source device according to Embodiment 3 of the invention.
Figure 11:
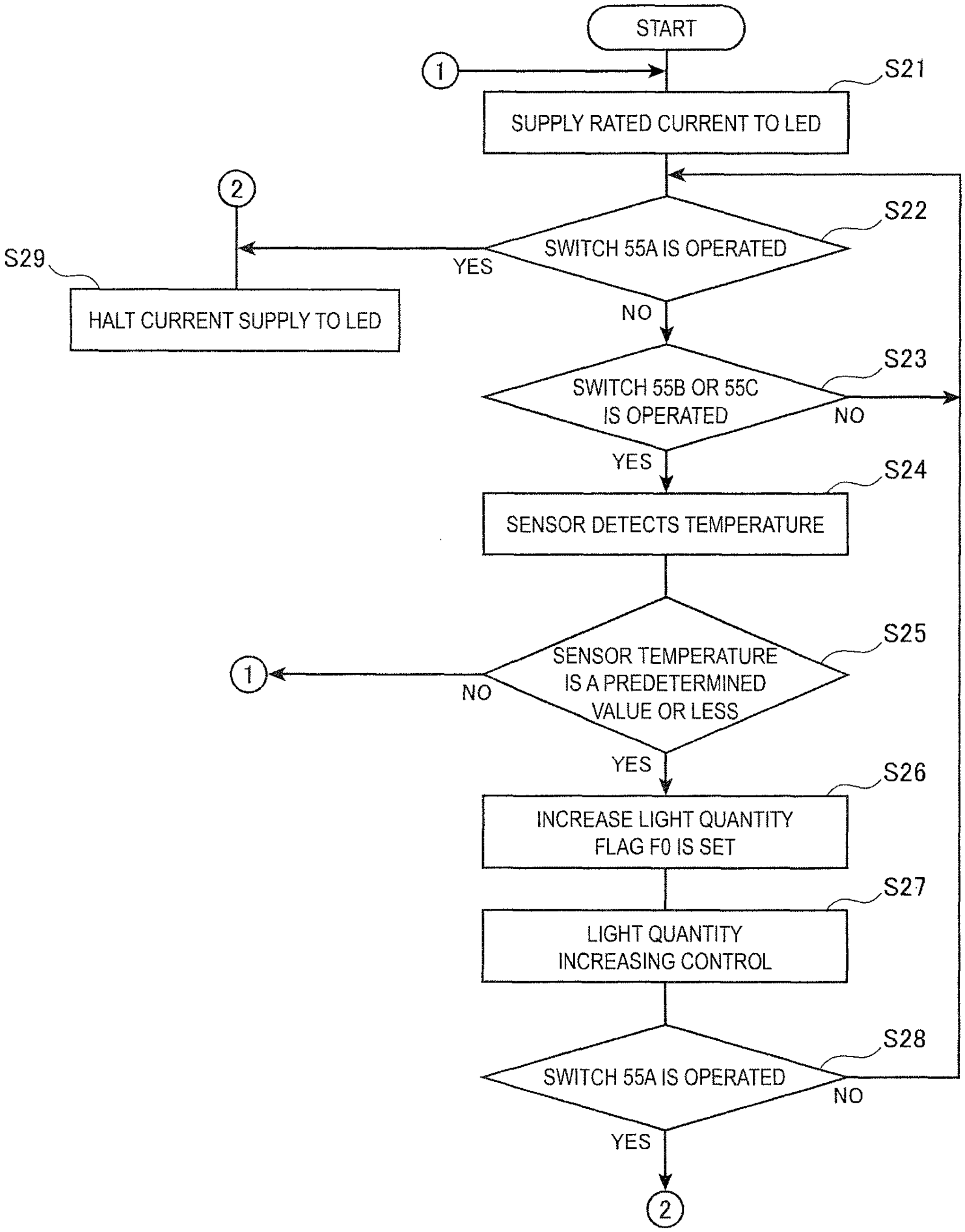
FIG. 11 is a flowchart illustrating a processing procedure for a control section to control lighting of an LED illumination section according to Embodiment 3 of the invention.

FIG. 10 is a block diagram illustrating an electric circuit of a medical light-source device according to Embodiment 3 of the invention, and each component in the circuit having the same function as in FIG. 8 is assigned the same reference numeral to omit descriptions thereof. In this Embodiment, a temperature sensor 63 by a thermistor or the like is provided for the temperature of the LED element of the LED illumination section 61. Further, as shown in the flowchart of FIG. 11, the processing procedure for the MPU to control lighting of the LED illumination section 61 is different from the processing procedure in FIG. 9, and will be described below.

When the switch 55A is operated, the MPU starts the processing procedure, and controls the current control circuit 62 so as to supply a rated value of current to the LED illumination section 61 (step S21). The current control circuit 62 is controlled by the MPU so that the average current value fed from the battery power supply section 60 to the LED illumination section 61 is a rated value.

Then, the MPU acquires a signal from the switch section 55, checks the operation of the switch 55A (step S22), and when the switch 55A is not performed, checks the operation of the switch 55B or switch 55C (step S23). When the switch 55B or switch 55C is not operated, the processing of from step S22 is repeated. Meanwhile, when the MPU identifies the operation of the switch 55A in step S22, the processing in step S29 is performed where the MPU controls the current control circuit 62 so as to halt the supply of current from the battery power supply section 60 to the LED illumination section 61 and halts the emission operation.

Meanwhile, when the MPU identifies the operation of either the switch 55B or switch 55C, the MPU captures an output from the temperature sensor 54 to detect the temperature (step S24), and determines whether the detected temperature is a predetermined temperature (for example, 80° C., or lower temperature with a margin included) (step S25). When the detected temperature is the predetermined temperature or less, the MPU sets the register R for an increase light quantity flag F0 corresponding to the operated switch 55B or switch 55C (step S26). The increase light quantity flag F0 is data to identify the operated switch 55B or 55C.

Subsequently, the MPU performs increase light quantity control corresponding to the content of the increase light quantity flag F0 (step S27). The MPU checks whether the MPU is instructed to halt emission by operation of the switch 55A in next step S28, and when the switch 55A is not operated, returns to the processing of from step S22. In the increase light quantity control, as in the processing procedure of FIG. 9, based on the content of the increase light quantity flag F0, the MPU controls the current control circuit 62 so as to increase the illumination quantity of the LED illumination section 61 corresponding to the operated switch 55B or switch 55C.

In this way, when the MPU detects in step S25 that the temperature detected by the temperature sensor 63 reaches the predetermined temperature in the state in which the illumination quantity of the LED illumination section 61 is increased, the MPU clears the increase light quantity flag F0 of the register R to perform the processing of step S21, switches the current supplied to the LED illumination section 61 to the rated value to finish the light quantity increasing control, and performs the processing of from step S22. Then, when the MPU identifies the operation of the switch 55A, the MPU controls the current control circuit 62 to halt the supply of current to the LED illumination section 61 (step S29). At the same time, the content of the register R is all cleared, and is in the initial state.

While the switch 55A is not operated, the MPU controls the current control circuit 62 so as to supply the rated current to the LED illumination section 61, and the LED illumination section 61 emits a normal quantity of light. Then, when the MPU identifies that the switch 55B or 55C is operated without the switch 55A being operated, the MPU performs the processing of step S24, captures an output from the temperature sensor 54, and determines whether the detected temperature exceeds the predetermined temperature (step S25). When the detected temperature is less than the predetermined temperature, the MPU sets the register R for an increase light quantity flag F0 corresponding to the operated switch 55B or switch 55C (step S26), and repeats again increase light quantity control. Accordingly, for a period during which the MPU confirms that the temperature of the THD element is less than the predetermined temperature in step S25, even after finishing increasing the light quantity, the MPU is capable of resuming increasing the light quantity.

Next, control of current supply to the LED illumination section 61 by the MPU in the control section 54 will be described below, with specific circuit configurations of the current control circuit 62 in FIGS. 8 and 10 shown. In addition, two configurations of the current control circuit 62 are exemplified in FIGS. 12 and 13, and the current control circuit 62 in either FIG. 12 or FIG. 13 may be used.

Figure 12:
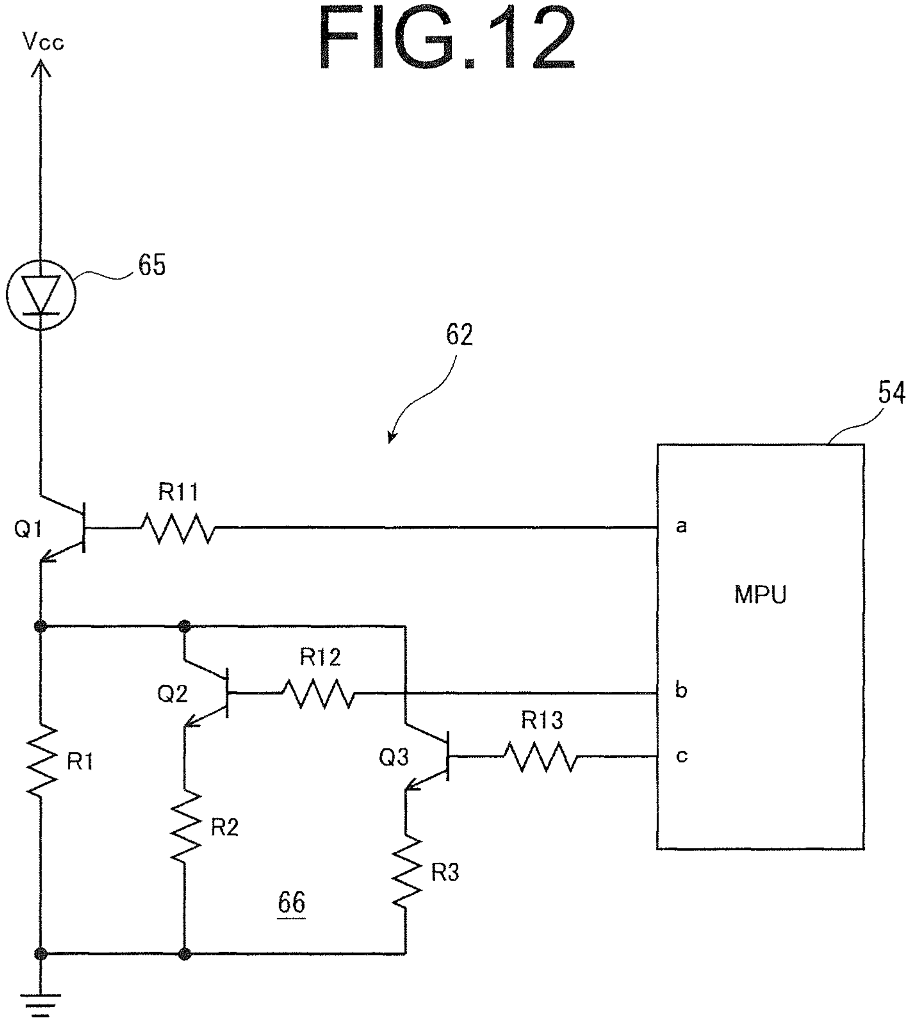
FIG. 12 is a diagram illustrating a specific circuit configuration showing an example of a current control circuit according to the Embodiment of the invention.

The current control circuit 62 as shown in FIG. 12 is constructed by connecting a driving transistor Q1 connected on its collector side to the LED element 65 of the LED illumination section 61, and a resistance circuit 66 connected to the emitter side of the transistor Q1 to power supply Vcc. Then, the MPU is connected at a port a to the base of the transistor Q1 through a resistance R11, and controls ON/OH of the transistor.

The resistance circuit 66 is comprised of a resistance R1 connected at its one end to the emitter of the transistor Q1 with the other end grounded, a series circuit of a transistor Q2 and resistance R2 parallel connected to the resistance R1, and a series circuit of a transistor Q3 and resistance R3 also parallel connected to the resistance R1. Then, the base of the transistor Q2 is connected to a port b of the MPU of the control section 54 through a resistance R12, the base of the transistor Q3 is connected to a port c of the control section 54 through a resistance R13, and the control section 54 controls ON/Or of each transistor. Herein, the resistance R11, resistance R12 and resistance R13 are provided to limit the base current to respective connected transistors.

A resistance value of the resistance circuit 66 is determined by a combined resistance value of the resistances R1, R2 and R3, and the current limitation resistance value is R1 in the normal state in which the transistor Q2 and the transistor Q3 are off, P1·R2/(P1+P2) when the transistor Q2 is on and the transistor Q3 is off, and is P1·R2·P3/(R1+R2+R3) when the transistor Q2 and the transistor Q3 are both on.

At this point, the resistance values of the resistances R1, P2 and R3 are set so that P1>P1·R2/(R1+R2)>R1·R2·P3/(R1+P2+R3), the supply current to the LED element 65 is the rated value when the resistance value is R1, the supply current when the current limitation resistance value is R1·142/(R1+P2) is an increase value, and the supply current when the current limitation resistance value is P1·P2·P3/(P1+P2+P3) is further increased. By this means, when the control section 54 switches off both the transistor Q2 and the transistor Q3, the rated value of current is supplied to the LED element 65 and the emission amount is normal. When the transistor Q2 is switched on, an increase value of current is supplied and the emission amount is increased. When both the transistor Q2 and the transistor Q3 are switched on, the supply current is larger, and the emission amount increases.

Accordingly, control for the control section 54 to switch off the transistor Q2 and the transistor Q3 corresponds to the processing for "supplying the rated current to the LED" in the processing procedure as described previously, control to switch on the transistor Q2 corresponds to "light quantity increasing control" of the time the switch 55B is operated, and control to switch on both the transistor Q2 and the transistor Q3 corresponds to "light quantity increasing control" of the time the switch 55C is operated.

In the current control circuit 62 of such a configuration, when the MPU switches on the transistor Q1 to supply power supply Vcc to the current control circuit 62, the current is fed to the LED element 65. At this point, since the control section 54 keeps the transistor Q2 and the transistor Q3 off, the rated current is fed to the LED element 65, and normal emission is performed. In addition, the MPU controls on/off of the transistor Q1 with a predetermined duty ratio to feed a predetermined current. Accordingly, the voltage applied to the LED element 65 is of a rectangular wave form, but is not limited to the rectangular wave, and may be substantially a half wave form by making the rising edge and the falling edge the shape of steps. By this means, it is possible to resolve abrupt illuminance changes.

Then, when the MPU switches on the transistor Q2 or switches on both the transistor Q2 and the transistor Q3 by the switch 55B or switch 55C being operated, the current corresponding to the current limitation resistance value of the resistance circuit 66 is fed to the LED element 65, and the element 65 emits. Accordingly, when the switch 55B or switch 55C is operated during the illumination operation of the LED illumination section 61 by the rated current, the MPU controls the LED illumination section 61 so that an amount of current exceeding the rated current is fed to the LED element 65 corresponding to the increase light quantity of the operated switch. Thus, the control section 54 controls the transistors Q1, Q2 and Q3 from the ports a, b and c of the MPU, and switches the emission amount of the LED element 65.

Controlling the emission operation of the LED illumination section 61 is not limited to the above-mentioned circuit configuration, and may be a pulse driving scheme for controlling a duty ratio corresponding to designation of the illumination intensity with a switch device on the circuit such as, for example, a transistor, MOSFET, etc. and thereby controlling a current fed to the LED illumination section 61.

Figure 13:
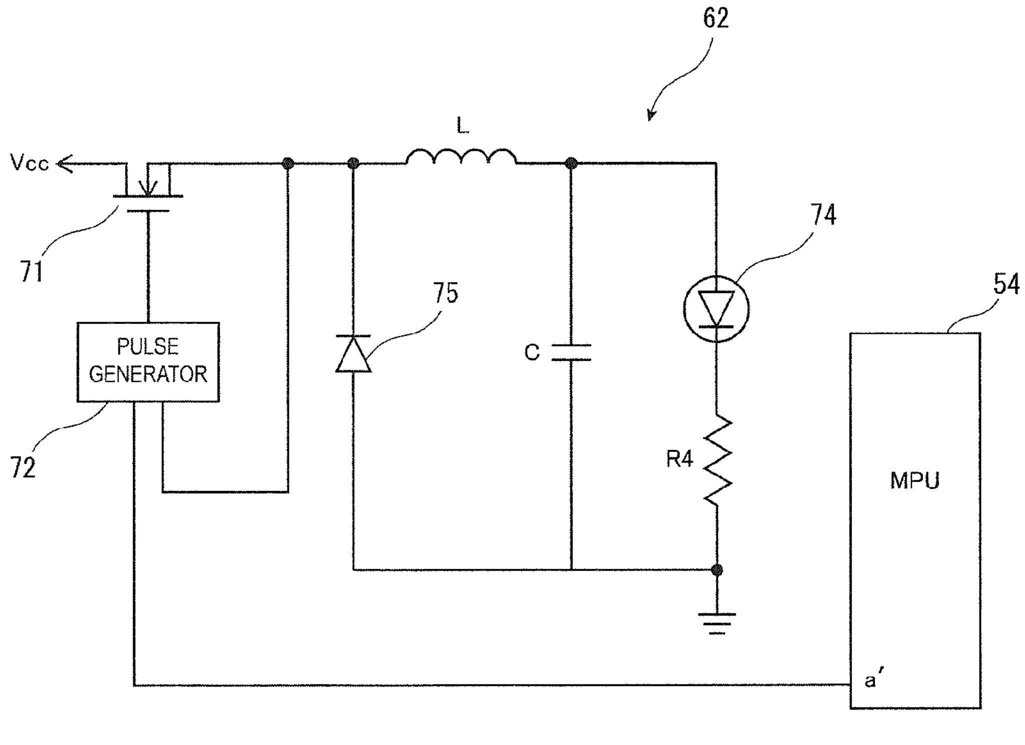
FIG. 13 is a diagram illustrating a circuit configuration in which a pulse driving scheme is adopted in the current control circuit according to the Embodiment of the invention.

FIG. 13 shows a configuration of the current control circuit 62 by the pulse driving scheme. In FIG. 13, for example, MOSFET is used as a switch device 71, and is connected so that a PWM (Pulse Width Modulation) signal from a pulse generator 72 is input to the gate side thereof. When the PWM signal becomes a high level by a control signal from a port a' of the MPU of the control section 54, the switch device 71 is turned on, the voltage of the battery power supply section 60 is applied, and the current flows from the input side to the load side.

To the load side of the switch device 71 are connected an LED 74 of the LED illumination section 61 and a protective resistance R4 which is grounded. In the prior stage, a smoothing circuit comprised of a coil L and a capacitor C is provided, and it is configured that a pulse output by switching operation is averaged and output. In the stage before the coil L, a diode 75 is provided to continue to supply a current to the coil L when the switch device 71 is switched off. By this means, by controlling the on time (off time) of the switch device 71, it is possible to efficiently adjust the current fed to the LED illumination section 61. Accordingly, in this case, the control section 54 is capable of increasing the light quantity of the LED illumination section 61 by performing control for changing the duty ratio of the pulse generator 72. In addition, the voltage applied to the LED element 74 is of a rectangular wave form, but is not limited to the rectangular wave, and may be substantially a half wave form by making the rising edge and the falling edge the shape of steps.

Corresponding to the operation of the switch 55B or switch 55C, the MPU performs control for changing the duty ratio so that the average current value fed to the LED illumination section 61 is changed from the rated value, and that the current of an increase value higher than the rated value is fed. Then, when either the switch 55B or 55C is operated, the supply current to the LED illumination section 61 is of an increase value exceeding the rated value, and the current fed when the switch 55B is operated is made higher than the current fed when the switch 55C is operated. The processing for the MPU to output a control signal from the port a' to the pulse generator 72 corresponds to the processing for "supplying the rated current to the LED" and "increase light quantity control" when the switch 55B or switch 55C is operated in the processing procedure.

In the current control circuit 62 with such a configuration, the control signal output from the port a' by the MPU is to designate the duty ratio to supply the rated value of the current to the LED illumination section 61, and when the switch 55B or 55C is operated, the MPU outputs a control signal for changing the duty ratio so as to supply an increase value of current corresponding to the increase light quantity of the operated switch.

In the medical light-source devices of above-mentioned Embodiments 2 and 3, in the light-source device by the LED element wearable on the body of the operator, only when the need for particularly increasing the light quantity arises, the current of the maximum value or less exceeding the rated value (continuous rated value) is fed over a predetermined period within the range in which the LED element does not deteriorate due to the effect of heating, and therefore, it is possible to increase the light quantity without using the complicated configuration. Accordingly, power supply is not consumed more than necessary, and it is possible to ensure long illumination time required for being used in an operation in the medical field.

Further, for example, in LED illumination devices used in hare illumination use, etc., the emission amount of the LED is adjusted in multiple stages, and either of the devices continuously emits with the adjusted emission amount. Therefore, it is assumed that the device produces heat correspondingly when the device is adjusted to an emission state of high output, and in preparation for extreme reductions in life due to sudden halt and/or deterioration by heat, it is necessary to take appropriate heat dissipation measures. However, such heat dissipation measures result in increases in the device size in the medical light-source device premised on the small size to be wearable on the body of the operator. Then, only in the case that the need for particularly increasing the light quantity arises, the current of the maximum value or less exceeding the rated value (continuous rated value) is fed over a predetermined period within the range in which the LED element does not deteriorate due to the effect of heat, the device thereby eliminates the need for a large capacity of battery and particular heat dissipation measures, and the small-sized medical light-source device is provided.

The LED illumination section 61 is worn on the body of the operator with the holder, is held with a binocular loupe, for example, and is worn on the head of the operator. Further, as in Embodiment 1, the battery power supply section 60 may be worn on part of the body of the operator. In this case, when the section 60 is worn on the waist of the operator with the battery holding belt 8 shown in FIG. 5, the control section 54 including the MPU and current control circuit 62 and the switch section 55 are integrated as a control unit 10 and attached to the battery holding belt 8 together with the battery power supply section 60, and the control unit 10 is configured to supply the driving current to the LED illumination section 61 via a code 42 to perform illumination operation. When the charger 6 with the plug inserted therein is connected to the outlet 41, the control unit 10 performs control for charging the battery power supply section 60, and is capable of performing illumination operation by the illumination section 61 while charging the battery power supply section 60.

Embodiment 4 of the invention will be described below. In this Embodiment, an acceleration sensor detects a motion of an operator, and the emission amount is controlled corresponding to the motion. In medical operations, it is assumed that the time with the need for applying a higher quantity of light to a part in the medical treatment such as cutting and suture of a blood vessel or minute portion and the like is almost 20% of the whole. Accordingly, by controlling to dim the LED illumination section 1 during a period except the time of almost 20%, it is possible to suppress consumption of the power supply.

Figure 14:
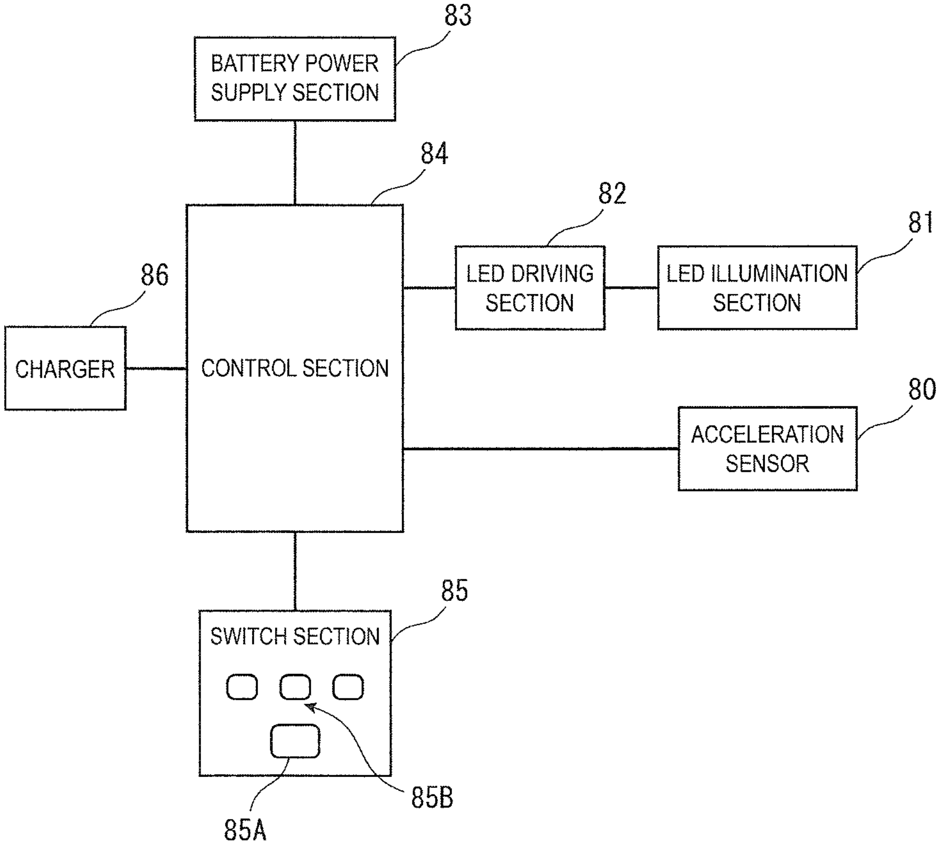
FIG. 14 is a block diagram illustrating an electric circuit of a medical light-source device according to Embodiment 4 of the invention.

Accordingly, the acceleration sensor is provided together with the LED illumination section in the holder to detect a motion of the operator. Then, for a period during which the acceleration sensor detects acceleration, the period is judged as being an operation period without the need for applying a higher quantity of light, and the LED illumination section 1 is controlled to dim. FIG. 14 is a block diagram illustrating a configuration of the electric circuit, and is comprised of an LED illumination section 81, LED driving section 82, battery power supply section 83, control section 84, switch section 85 provided with a power supply ON/OFF switch 85A and three selection switches 85B to adjust the illumination intensity of the LED illumination section 81 to high, middle and low, AC adopter as a charger 86 to charge the battery power supply section 83, and acceleration sensor 80.

As the acceleration sensor 80, it is possible to use various kinds including the mechanical type, optical type and semiconductor type, and as a medical light-source device, the semiconductor type is optimal in terms of making the size smaller. Particularly, the semiconductor type is more preferable when the holder is a binocular loupe, cap or head band put on the head of the operator.

Figure 15:
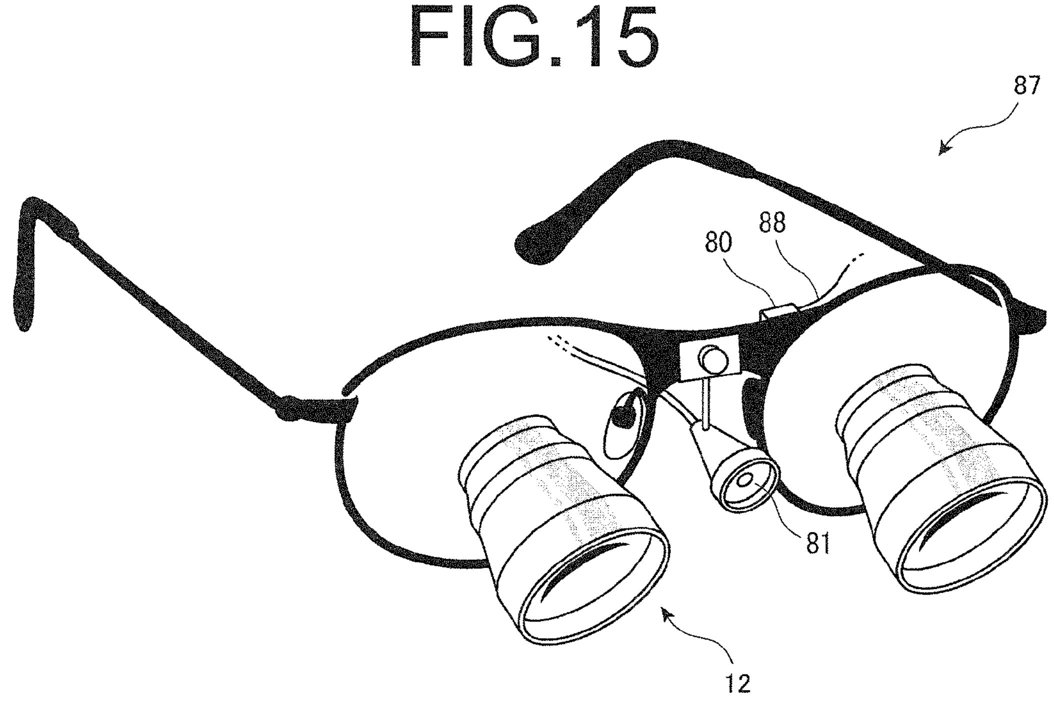
FIG. 15 is an explanatory view when a holder according to Embodiment 4 of the invention is a binocular loupe.

FIG. 15 shows an example in which the acceleration sensor 80 is attached to a binocular loupe 87, and the acceleration sensor 80 detects a vibration by a motion of the head of the operator to transform into an electric signal, and transmits the signal to the control section 84 with a signal cable 88. The acceleration sensor 80 is bonded to the binocular loupe 87 with an adhesive tape or the like.

By switching on the power supply ON/OFF switch 85A, when a power supply ON signal is input from the switch section 85, the control section 84 controls the emission operation of the LED illumination section 81 through the LED driving section 82. Then, by operating the selection switch 85B, when an illumination intensity selection signal is input from the switch section 85, the control section 84 controls the LED driving section 82 so that a constant current associated with the intensity of light designated at this point is applied to the LED illumination section 81.

When the acceleration sensor 80 detects acceleration of a predetermine value or more while the control section 84 performs passage control on the LED illumination section 81, the control section 84 controls the LED driving section 82 so as to reduce illuminance of the LED illumination section 81. Then, when the acceleration is less than the predetermined value, the control section 84 controls the LED driving section 82 so as to emit with the intensity of light designated by the selection switch 85B.

In the above-mentioned configuration, in the medical treatment such as cutting and suture of a blood vessel or minute portion in an operation and the like, since the operator focuses light on the treatment target portion while fixing the LED illumination section 81, the acceleration, which is detected by the acceleration sensor 80 held by the holder together with the LED illumination section 81, is small, and the control section 84 causes the section 81 to emit with the intensity required by the operator. Meanwhile, even in the operation, during the time the operator does not perform the medical treatment directly, since the operator makes a large motion such that the operator shifts the entire body by preparation working and the like, the head vibrates, and the acceleration detected by the acceleration sensor 80 is large. Then, when the acceleration is a predetermined value or more, the control section 84 controls the LED driving section 82 to reduce illuminance of the LED illumination section 81, and effective use of the battery power supply section 83 is thereby made. At this point, when the acceleration detected by the acceleration sensor 80 is the predetermined or more, illumination of the LED illumination section 81 may be halted.

Further, also in the configuration of this Embodiment, the battery power supply portion 83 may be also worn on part of the body of the operator as in Embodiment 1. In this case, when the section 83 is worn on the waist of the operator with the battery holding belt 8 as shown in FIG. 5, the control section 84 and the switch section 85 are integrated into a control unit 10 and attached to the battery holding belt 8 together with the battery power supply section 83.

Such control of illuminance of the LED illumination section 81 using the acceleration sensor is applicable to the configurations of Embodiments 2 and 3 as previously described. For example, when the second switch 55B or 55C is operated, the average current value fed to the LED illumination section 61 (FIG. 8 or FIG. 10) is changed to flow an increase value of current higher than the rated value, and high-output emission control is started, the MPU monitors an acceleration detection signal from the acceleration sensor periodically by timer interrupt. Then, when the acceleration exceeds a predetermined value, the MPU performs control for reducing the average current value fed to the LED illumination section 61 to the rated value. In this way, even when the second switch 55B or 55C is operated, in the case that the operator does not actually perform the medical treatment for focusing light on a treatment target part, the control section is capable of returning to normal emission control immediately, being effective in preventing power consumption of the battery power supply section 60 (FIG. 8 or FIG. 10) and in protecting the LED element.

As specifically described above, in the invention, a large capacity of battery power supply is secured by wearing the battery on the body, the LED element is caused to emit with high output for a certain time by operating the switch, the acceleration switch is provided to reduce illuminance for a period judged as not having the need for applying a high intensity of light from the motion of the operator even during the operation period, and the medical power supply is thereby capable of performing illumination for a long time.

The illumination time is increased by adopting each of these three methods alone, but as described above, by combining the methods as appropriate, it is possible to exhibit illumination for a longer time.

Figure 16:
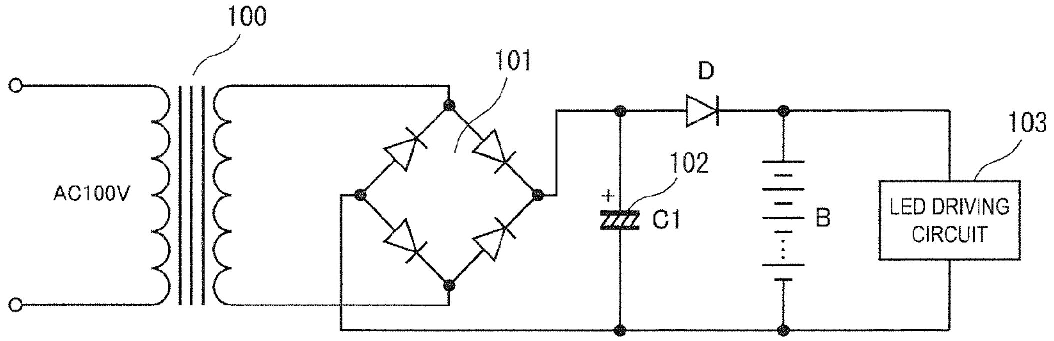
FIG. 16 is a diagram illustrating a circuit configuration of a power supply section when power is supplied from an AC commercial power supply to the medical light-source device of the invention.

Further, the medical light-source device according to the invention is capable of being used while being connected to an AC commercial power supply. In this case, the LED is driven by a 12V DC power supply transformed from commercial power supply AC 100V, and as shown in FIG. 16, it is configured that a commercial power supply is connected to an all-wave rectifier circuit 101 via a transformer 100, generated all-wave rectification is smoothed in a smoothing circuit 102, and that the generated direct current is supplied to an LED driving circuit 103.

Then, the smoothing circuit 102 is connected to a battery power supply section B through a diode D for preventing a reverse flow. Accordingly, when a situation occurs such that power supply is halted by a power failure or the AC power supply code being removed, power supply to the LED driving circuit 103 is automatically changed to the battery power supply section B, and illumination of the LED is thus continued.

Thus, also in the configuration where power is supplied from a commercial power supply, provided is the medical light-source device capable of coping with a long-duration power failure even when the power supply is changed to the battery power supply B, by adopting control for causing the LED element to emit with high output for a certain time by operating the switch, and control for reducing illuminance for a period judged as not having the need for applying a high intensity of light from the motion of the operator even during an operation, using the acceleration switch, as described above.

Further, in order to obtain long-duration illumination while preventing the LED element from producing heat, it is also effective cooling the LED element using a fan. Currently, extremely-compact brushless DC fan motors exist which are of tens of millimeters square with a thickness of several millimeters, and further, are sufficient in small capacity ranging from about 3V to 5V. By using such a compact fan, it is possible to incorporate the fan into the housing of the LED illumination section to be worn on the body of the operator.

Figure 17:
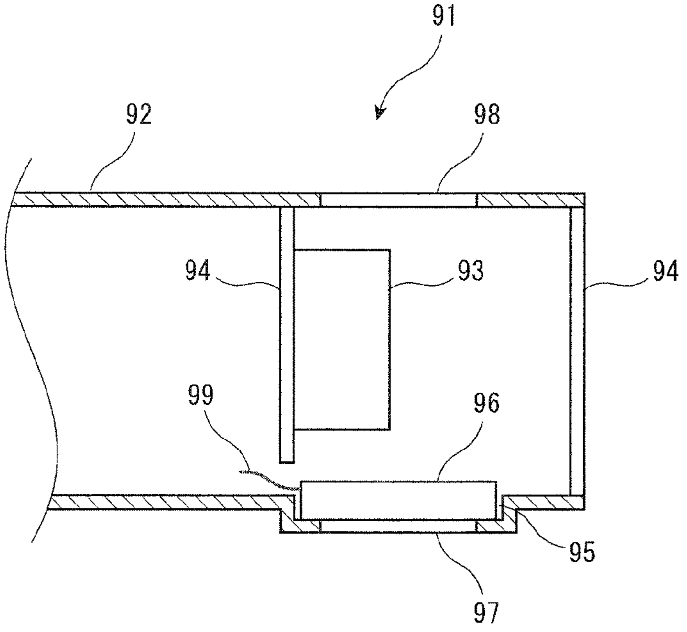
FIG. 17 is a diagram showing a sectional side elevation of a configuration of the LED illumination section with a built-in cooling fan.

FIG. 17 shows a configuration of an LED illumination section 91 with a compact fan incorporated thereinto, and the LED illumination section 91 stores an LED unit 93 inside a cylindrical housing 92. The LED unit 93 has a substrate 94 with the LED element mounted thereon, and the substrate 94 is attached to the inner wall of the housing 92, and is thereby fixed into the housing 92. Then, light emitted from the LED element is applied to the outside through a lens 94 forming a cap portion of the housing 92. Further, in part of the side face of the housing 92 is formed a concave portion 95 of the size that accommodates the compact fan 96 of the above-mentioned dimensions, for example.

The compact fan 96 is an axial-flow type fan, forms a flow of air between an inlet 97 provided on the bottom of the concave portion 95 and an exhaust opening 98 provided on the side face of the housing 92 to be opposed to the inlet 97, and cools the TFT unit 93. Then, power is supplied to the compact fan 96 via a lead wire 99 from the battery power supply section to supply power to the LED illumination section 91.

The present invention is not limited to the above-mentioned Embodiments, various modifications thereof can be made based on the subject matter of the invention, and the modifications are not excluded from the scope of the invention.

DESCRIPTION OF SYMBOLS

1, 61, 81, 91 LED illumination section
3, 60, 83 Battery power supply section
4, 54, 84 Control section
6 Charger
7 Holder
8 Battery holding belt
10 Control unit
55 A First switch
55B Second switch
63 Temperature sensor
80 Acceleration sensor
92 Housing of the LED illumination section
96 Fan

What is claimed is:

1. A medical light-source device adapted to be worn on a body of an operator to apply light to a target portion of a medical treatment, comprising:
- an LED illumination section having an LED element;
- a holder adapted to put the LED illumination section on a head of the operator;
- a battery power supply section that supplies power to the LED illumination section;
- a charger having an AC adaptor adapted to connect to a commercial power supply for charging the battery power supply section;

- a battery holding belt adapted to put the battery power supply section and the charger on the body of the operator; and
- an acceleration sensor provided in the holder for detecting a motion of the operator,
- wherein a control section performs control for reducing illuminance of the LED illumination section when the acceleration sensor detects acceleration of a predetermined value or more.

2. The medical light-source device according to claim 1, wherein the LED illumination section is adapted to receive power supplied from the commercial power supply through the AC adaptor while the AC adaptor is connected to the commercial power supply in use, and
- the battery power supply section is configured so that when the commercial power supply fails or connection to the AC adaptor is interrupted, the battery power supply section supplies power to the LED illumination section without instantaneous interruption of the illumination.

3. The medical light-source device according to claim 1, wherein the holder is a binocular loupe adapted to be worn on the head of the operator.

4. The medical light-source device according to claim 1, wherein the holder is a cap or a head band adapted to be put on the head of the operator.

5. The medical light-source device according to claim 1, wherein the LED illumination section has an installation section to be detachably attached to the holder.

6. The medical light-source device according to claim 1, wherein the battery holding belt is a belt adapted to be wound around a waist of the operator.

7. The medical light-source device according to claim 1, wherein the control section controls lighting of the LED illumination section by pulse driving with a duty ratio corresponding to designation of intensity of illumination together with on/off of the LED illumination section.

8. The medical light-source device according to claim 1, wherein a switch section and the control section are integrated to form a control unit, and the control unit is held with the battery holding belt.

9. The medical light-source device according to claim 1, wherein the holder is attached a fan to cool the LED illumination section.

10. The medical light-source device according to claim 9, wherein the fan is incorporated into a housing of the LED illumination section to cool the LED element.

11. The medical light-source device according to claim 1, further comprising a LED driving section connected to the control section so that the control section controls the illumination operation of the LED illumination section through the LED driving section.

12. The medical light-source device according to claim 1, wherein the battery holding belt has a switch section to switch on/off the LED illumination section and to adjust intensity of illumination of the LED element.

13. The medical light-source device according to claim 12, wherein the control section is connected to the switch section to receive an input from the switch section to control on/off the LED illumination section and an amount of current supplied to the LED illumination section corresponding to the intensity of illumination according to the switch section.

* * * * *